(12) United States Patent
An

(10) Patent No.: US 6,461,377 B1
(45) Date of Patent: Oct. 8, 2002

(54) PORTABLE THERAPEUTIC DEVICE

(76) Inventor: Byung-Yul An, 106-105, Karam Apt., 735, Ilwon-Dong, Kangnam-ku Seoul (KR)

( * ) Notice: Subject to any disclaimer, the term of this patent is extended or adjusted under 35 U.S.C. 154(b) by 0 days.

(21) Appl. No.: 09/601,837

(22) PCT Filed: Feb. 4, 1999

(86) PCT No.: PCT/KR99/00055

§ 371 (c)(1),
(2), (4) Date: Aug. 4, 2000

(87) PCT Pub. No.: WO99/39764

PCT Pub. Date: Aug. 12, 1999

(30) Foreign Application Priority Data

| Feb. 6, 1998 | (KR) | 98-1315 |
| Apr. 23, 1998 | (KR) | 98-6475 |
| Sep. 11, 1998 | (KR) | 98-17566 |

(51) Int. Cl.[7] ............................. A61F 7/12; A61F 2/00
(52) U.S. Cl. ............................ 607/96; 607/100; 600/9; 601/15; 601/66
(58) Field of Search ......................... 607/96, 98, 100, 607/108–112; 600/9, 11, 13, 15; 601/15, 66, 67, 69, 70, 113

(56) References Cited

U.S. PATENT DOCUMENTS

| 1,844,247 A | * | 2/1932 | Freemon | 392/409 |
| 4,915,110 A | | 4/1990 | Kitov | |
| 5,097,828 A | * | 3/1992 | Deutsch | 604/113 |
| 5,327,886 A | * | 7/1994 | Chiu | 601/15 |
| 5,894,067 A | * | 4/1999 | Kim | 252/301.36 |
| 6,001,055 A | * | 12/1999 | Souder | 600/9 |
| 6,102,875 A | * | 8/2000 | Jones | 601/112 |

FOREIGN PATENT DOCUMENTS

| CN | 91107439.2 | 1/1993 |
| CN | 95107504.7 | 1/1997 |
| CN | 95119856.4 | 8/1997 |
| CN | 94119284.9 | 8/2000 |

* cited by examiner

Primary Examiner—Roy D. Gibson
(74) Attorney, Agent, or Firm—Banner & Witcoff, Ltd.

(57) ABSTRACT

A portable therapeutic device radiates far infrared rays from Macbanseok received therein and applies electric stimulation to the body by means of an electric needle, in addition to generating magnetic vibration through rotation of two permanent magnets having magnetic polarities different from each other. The portable therapeutic device smoothes blood circulation by means of the magnetic vibration, and may relieve neuralgia and arthritis by applying the electric stimulation to a pain area of the human body. Also, the portable therapeutic device can easily be worn on a desired area of the human body by using a band.

15 Claims, 7 Drawing Sheets

PORTABLE THERAPEUTIC DEVICE

TECHNICAL FIELD

This invention relates to a portable therapeutic device, and more particularly, to a portable therapeutic device which radiates far infrared rays from Macbanseok received therein and applies electric stimulation to the body by means of an electric needle, in addition to generating a magnetic vibration through rotation of two permanent magnets having magnetic polarities different from each other, in order to eliminate cholesterol in blood and smooth the blood circulation.

BACKGROUND ART

For several decades interest in the application of non-traditional treatment techniques for the relief of body pain and other organic irregularities has increased. An important area of these non-traditional techniques is called Diathetic Medicine, which is related to the constitutional tendency of the human body to suffer from certain diseases.

Magnets, Macbanseok, and an electric stimulating devices are used in the non-traditional techniques.

Generally, magnetism smoothes blood circulation by stimulating blood vessels containing hemoglobin iron, and eliminates cholesterol. A therapeutic device using a permanent magnet is available to generate the magnetism.

However, the conventional therapeutic device is constructed by simple installing the permanent magnet on a desirable part thereof in contacting with the skin. Because the permanent magnet is secured to the device, a magnetic-impacting effect of the permanent magnet is insufficient and thus the utility value of the therapeutic device deteriorates.

A pulse-magnetic therapeutic device used for physiotherapy of a patient with a fracture has a good magnetic-impacting effect, but is inconvenient to carry for frequent use because the device is quite big in size and furthermore it is expensive.

The Macbanseok provides a human body with vital power restoration such as organic activation and facilitation of blood circulation, and has a considerable effect on neuralgia, rheumatism, lumbago, and arthralgia etc.

The Macbanseok (English transliteration of a Korean word) is a rock, such as granite porphyry, quartz porphyry and diolite porphyry, which comprises barley-type discriminating spots. Also, the Macbanseok is a base rock formed from submarine resources such as a lava layer, sea weed, marine animals and shell, and rock salt which were deposited and later upheaved over several hundred millions. This rock radiates various elements and far infrared rays. Also, the Macbanseok is a raw material of bio-ceramic.

A variety of devices and apparatus are know to provide stimulation to the energy points of the body, through the application of small electricity on certain points of the skin. Several mechanical and electromechanical apparatus have been developed that allow one to massage the energy points on the skin.

U.S. Pat. No. 4,915,110 (issued to Zeev Kitov on Apr. 10, 1990) discloses a therapeutic electrostatic device.

However, the therapeutic devices are expensive and inconvenient to carry and use.

Accordingly, a portable therapeutic device integrally is required which has integrally a variety of functions such as a magnetic vibration function, electric stimulation function, and a far infrared rays applying function, plus is each to carry and use.

DISCLOSURE OF INVENTION

To solve the above problems, it is the first object of the present invention to provide a portable therapeutic device which integrally has an alternate magnetic generating means, far infrared rays generating means using Macbanseok pieces, and an electricity generating means for electric stimulation, in order to prevent certain diseases and facilitate blood circulation of the human body.

It is a second object of the present invention to provide a portable therapeutic device which is convenient to carry and can be easily worn on a pain area of the body.

To obtain these objects, a portable therapeutic device according to the present invention comprises:

a first case;

a second case joined with the first case;

a power supply means mounted in the first case and the second case and having a battery for supplying power, a first terminal contacting with one end of the battery, and a second terminal contacting with the other end of the battery;

a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means;

an electricity generating means which includes a pressure button, an electricity generating source generating electricity through push of the pressure button, an electricity output terminal formed at one portion of the electricity generating source for emitting the electricity, an electric needle projectingly formed outside the first case for directly transmitting the electricity to the human body, and an electric line transmitting the electricity from the electricity output terminal to the electric needle; and a means for generating far infrared rays through internal heat produced by the operation of the driving motor in order to facilitate blood circulation of human body.

The portable therapeutic device generates alternate pulse-magnetic vibration by biasedly rotating two permanent magnets with the surfaces of both magnets opposite to the skin having an N-pole and an S-pole respectively, while still having a simple construction and convenience to carry.

BRIEF DESCRIPTION OF DRAWINGS

This invention will be better understood and its various objects and advantages will be more fully appreciated from the following description taken in conjunction with the accompanying drawings, in which.

BEST MODE FOR CARRYING OUT THE INVENTION

Hereinafter, preferred embodiments according to the present invention will be described in detail with reference to the drawings.

Embodiment 1

Figure 1:
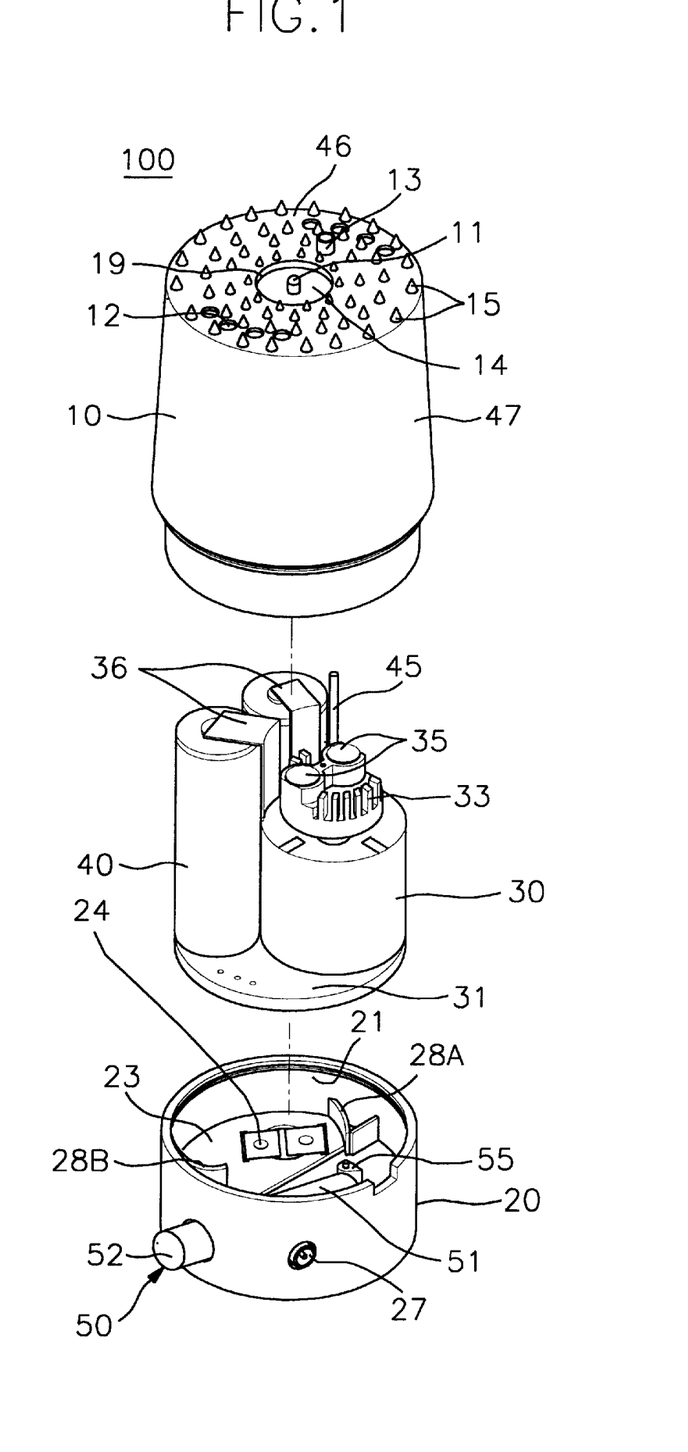
FIG. 1 is an exploded perspective view of a portable therapeutic device according to a first preferred embodiment of the present invention.

FIG. 1 is an exploded perspective view of a portable therapeutic device according to a first preferred embodiment of the present invention.

As shown in FIG. 1, the portable therapeutic device 100 according to the first preferred embodiment of the present invention includes a first case 10 and a second case 20 joined to the first case 10. The first case 10 has a top surface 46 and a cylindrical side wall 47 vertically elongated from a periphery of the top surface 46. Also, the first case 10 rotates about the second case 20 by a desirable scope in a clockwise direction or in a counterclockwise direction.

A central hole 19 and a plurality of penetrating holes 12 for directly applying far infrared rays on the human body are installed on the top surface 46 of the first case 10. A translucent plate 14 having a radiation bulb 11 for displaying the operation of the therapeutic device and transmitting moxibustion-heat on the skin is installed at the central hole 19. The translucent plate 14 is made from a plastic of insulating material. Also, a plurality of acupressure bosses 15 for providing a finger-pressure effect on a muscle and an electric needle 13 for applying the instantaneous electric stimulation on the human body are installed on the top surface 46 of the first case 10.

The second case 20 has a first stopper 28A and a second stopper 28B, which are curvedly projected from an inner periphral wall 21 of the second case 20 toward the center of the second case 20. A supporting plate 23 is mounted between the first stopper 28A and the second stopper 28B, and second terminal 24 connected with a battery 40 for flowing electricity is biasedly installed on the supporting plate 23.

The portable therapeutic device 100 comprises the battery 40 for supplying power, a first terminal 36 contacting with one end of the battery 40, and a second terminal 24 contacting with the other end of the battery 40.

Also, an electricity generating means 50 for generating the electricity and an electric connector 27 connected to the second terminals 24 by the electric line are mounted in the second case 20. The electric connector 27 is used for operating a portable therapeutic device 100 through an outside power source (not shown) instead of the battery 40. The electricity generating means 50 includes a pressure button 52 projected outside the second case 20, an electricity generating source 51, an electricity output terminal 55, and an electric line 45 connected to the electricity output terminal 55. The electric line 45 connects the electricity output terminal 55 with the electric needle 13.

Furthermore, a driving motor 33 mounted on a cover 31 and operating through the battery 40 and a rotating body 30 installed on the axle of the driving motor 30 are received in the first case 10. One pair of permanent magnets 35 having different magnetic polarities is biasedly installed on the rotating body 33, and a first terminal 35 with which the other end of the battery 40 contacts is provided on a periphery of the driving motor 30.

Preferably, several pairs of permanent magnets 35 may be provided in the therapeutic device.

Figure 2:
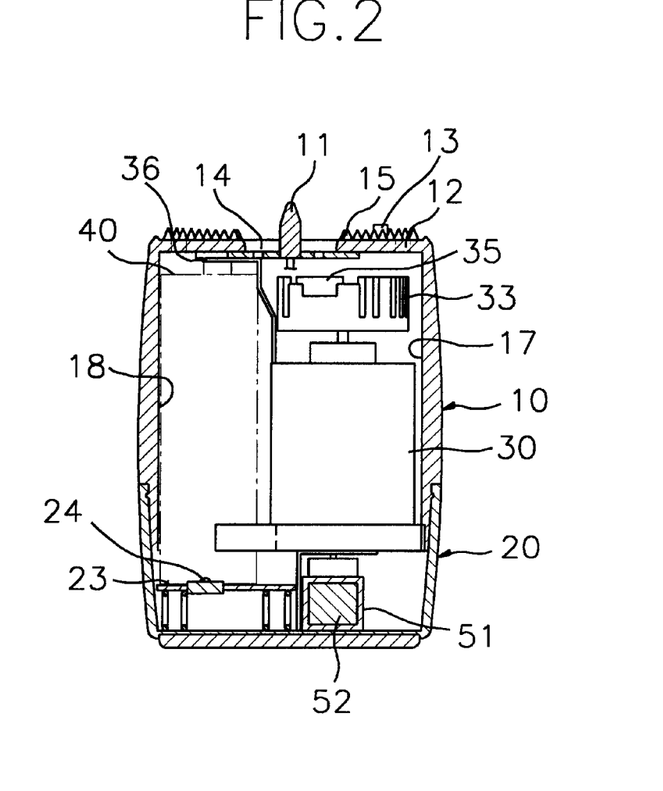
FIG. 2 is a longitudinal sectional view of the portable therapeutic device according to FIG. 1.
Figure 3:
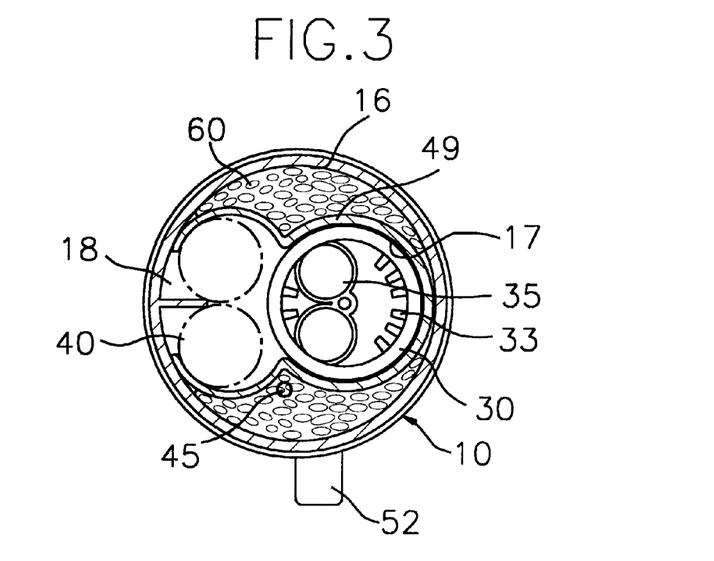
FIG. 3 is a transverse sectional view of the portable therapeutic device according to FIG. 1.

FIG. 2 is a longitudinal sectional view of the portable therapeutic device according to FIG. 1, and FIG. 3 is a transverse sectional view of the portable therapeutic device according to FIG. 1.

As shown in FIG. 2 and FIG. 3, the portable therapeutic device 100 according to the first preferred embodiment of the present invention has a cylindrical cross-section, and the first case 10 includes inner separating walls 49 for forming a magnetic vibration generating means housing 17 for accommodating the driving motor 30 and the rotating body 33, a battery housing 18 for accommodating the battery 40, and a Macbanseok housing 16 for accommodating Macbanseok pieces.

The Macbanseok is finely broken into pieces 60 which are contained within the Macbanseok housing 16 due to the cover 31.

Hereinafter, the operation of the first preferred embodiment according to the present invention will be described.

Figure 4:
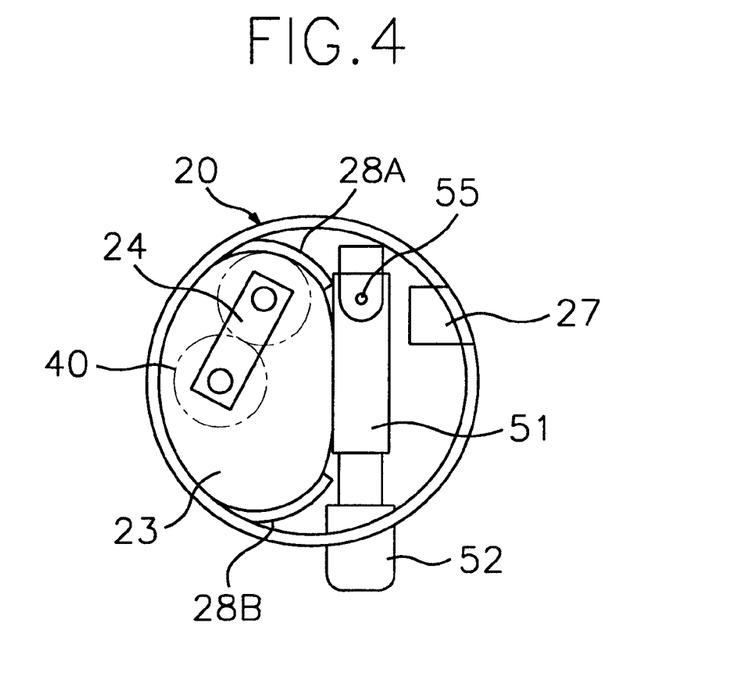
FIG. 4 is a top view of a second case of the portable therapeutic device according to the first preferred embodiment of the present invention, in which a battery is placed on a second terminal.

FIG. 4 is a top view of a second case of the portable therapeutic device according to the first preferred embodiment of the present invention, in which a battery is placed on a second terminal.

Figure 5:
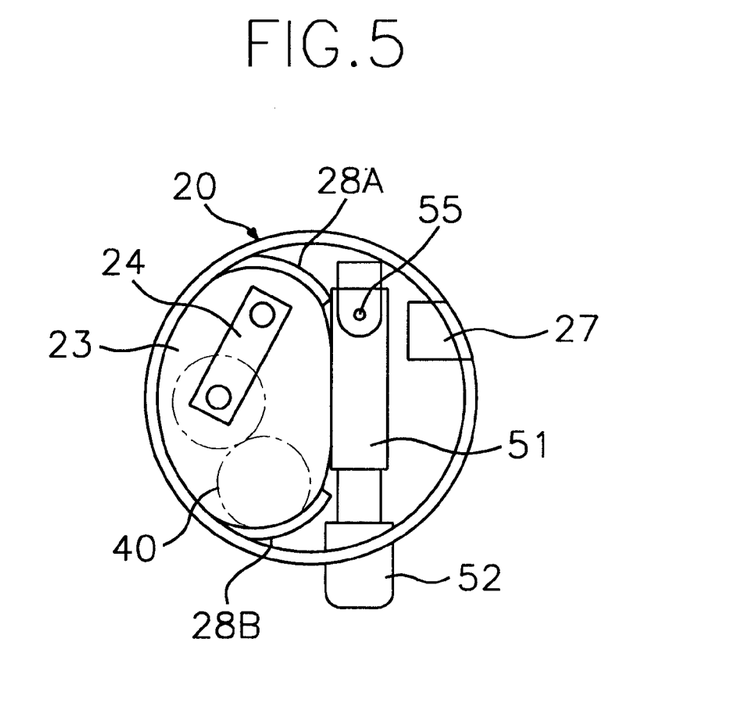
FIG. 5 is a top view of the second case of the portable therapeutic device according to the first preferred embodiment of the present invention, in which the battery is not placed on the second terminal.

As shown in FIG. 4, in a magnetic vibration mode, when the first case 10 rotates about the second case 20 in clockwise direction from a non-operating state of the driving motor 30 in FIG. 5, the battery 40 contacts with the second terminal 24 and thus the driving motor 30 operates due to transmitting of the power. At this time, the first case 10 does not rotate any longer due to the first stopper 28A. By the operation of the driving motor 30, the rotating body 33 rotates, and thereby vibration is generated by both permanent magnets biasedly installed on the rotation body 33. The permanent magnets 35 rotate and simultaneously generate magnetic force different from each other, and thus vibrate hemoglobin iron, positive ion, and negative ion in the blood by a pushing force and an attracting force of the magnets 35 to eliminate waste products deposited in blood vessels. Accordingly, elimination of the waste products facilitates blood circulation and metabolism.

When the magnetic force is applied to the human body, the vibration is generated simultaneously, resulting in doubling the effect of the magnetic force. Also, the pressure bosses 15 formed on top surface 46 of the first case 10 have an acupressure effect by contacting a pain area of the human body, and repeated stimulation is conducted by the vibration of the rotating body 33.

FIG. 5 is a top view of the second case of the portable therapeutic device according to the first preferred embodiment of the present invention, in which the battery is not placed on the second terminal.

As shown in FIG. 5, when the first case 10 rotates about the second case 20 in a counterclockwise direction to stop the operation of the driving motor 30, battery 40 received in the first case 10 rotate to be separated from the second terminals 24. Accordingly, due to non-transmission of the power, the operation of the driving motor 30 halts. At this time, the battery 40 does not rotate any longer because of the second stopper 28B.

The portable therapeutic device 100 operates by connecting the outer power source (not shown) to the electric connector instead of the battery 40.

The Macbanseok pieces 60 loaded into the Macbanseok housing 16 radiate the far infrared rays in proportion to temperature elevation in the therapeutic device 100 according to operation of the radiation bulb 11 and the driving motor 30, and the far infrared rays are transmitted on the pain area of the human body through the penetrating holes 12. The penetrating hole 12 allows a large number of the far infrared rays to be effectively transmitted to the pain area.

Furthermore, for relief of neuralgia, anthritis, myalgia, and facial paralysis, facilitation of the blood circulation, and recovery from body fatigue, the electric needle 13 is used. When the electric needle 13 contacts the pain area and the pressure button 52 is pressed, the electricity is generated from the electricity generating source 51 and is transmitted from the electricity output terminal 55 via electric line 45 to the electric needle 13. Accordingly, the electricity transmitted from the electric needle 13 applies the electric stimulation to the pain area of the human body, resulting in providing a general acupuncture effect.

Embodiment 2

Figure 6:
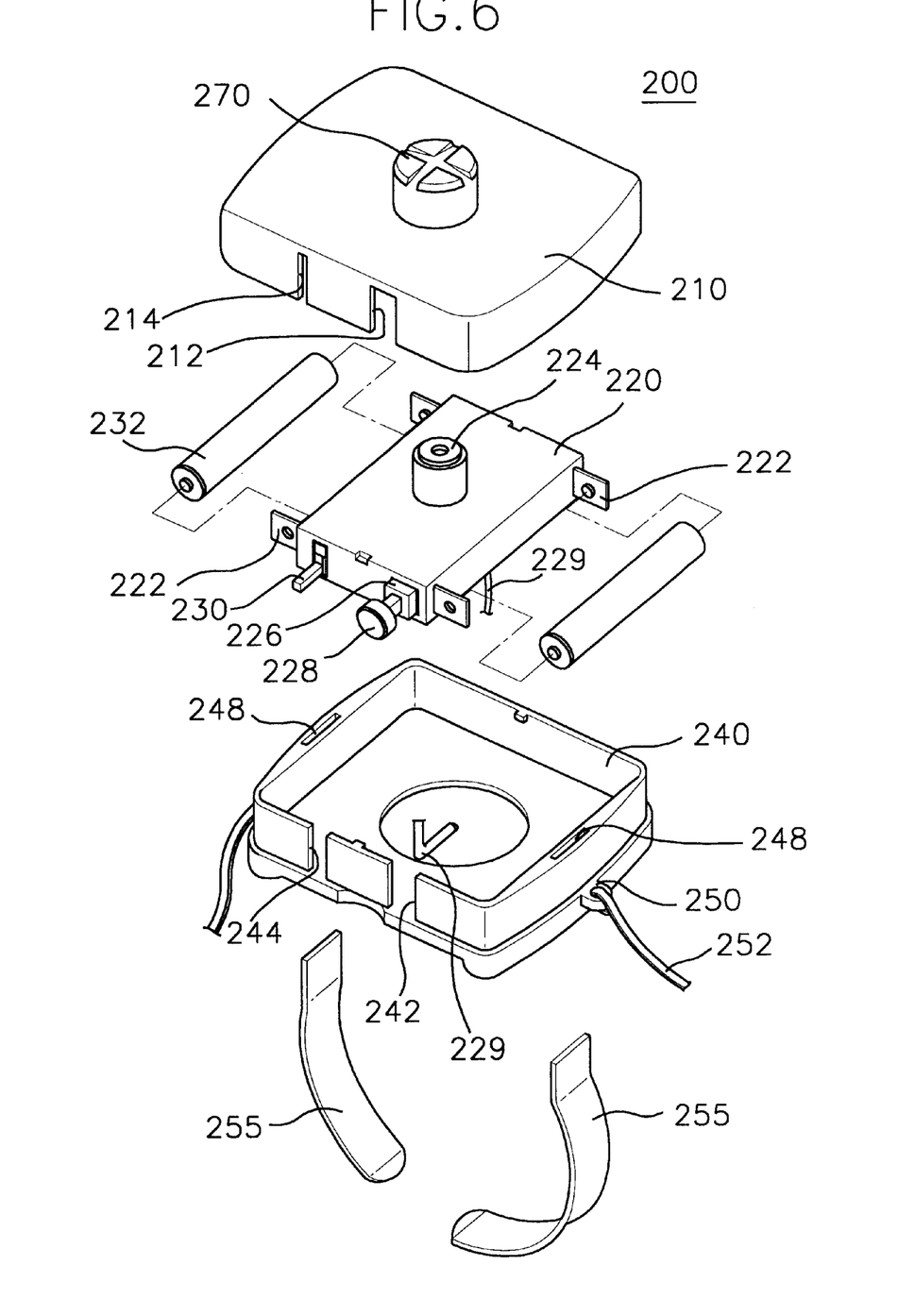
FIG. 6 is an exploded perspective view of a portable therapeutic device according to a second preferred embodiment of the present invention.

FIG. 6 is an exploded perspective view of a portable therapeutic device according to a second preferred embodiment of the present invention.

As shown in FIG. 6, the portable therapeutic device according to the second preferred embodiment of the present invention has a rectangular cross section, and includes a first case 210, a second case 240 fitted with the first case 210, and an internal case 220 mounted between the first case 210 and the second case 240.

The internal case 220 has a driving motor 224 in the central portion and an on/off switch 230 at a side wall. An electricity generating source 226 and a pressure button 228 is installed in the internal case 220, and the pressure button 228 is projected outside so that a user can press the pressure button 228 to generate the electricity. Also, an electric line 229 for transmitting the electricity is connected to one end portion of the electricity generating source 226. A reference number 270 indicates a housing for receiving the driving motor 224.

An electric terminal 222 for fitting a battery 232 is mounted on both side walls of the internal case 220 respectively.

Two recesses 212,214 for inserting the pressure button 228 and the on/off switch 230 respectively are formed at a side wall of the first case 210, and two recesses 242,244 for inserting the pressure button 228 and the on/off switch 230 respectively are formed at a side wall of the second case 240.

Eyes 250 for connecting loop 252 and slits 248 for separately inserting a pair of bending plates 255 are integrally formed at both side walls of the second case 240.

Figure 7:
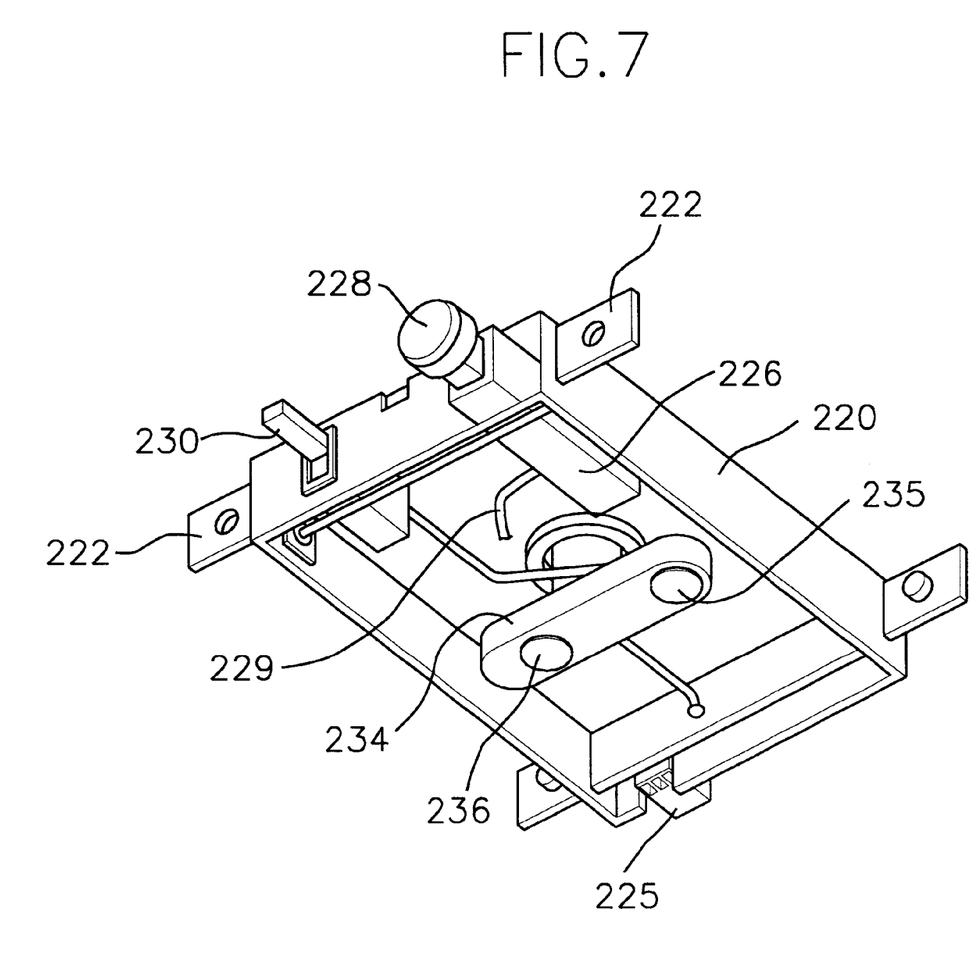
FIG. 7 is a perspective view of an inner case of the portable therapeutic device according to the second preferred embodiment of the present invention.

FIG. 7 is a perspective view of an inner case of the portable therapeutic device according to the second preferred embodiment of the present invention.

As shown in FIG. 7, a rotating body 234 installed on an axle of the driving motor 224 is provided in the internal case 220. One pair of permanent magnets 235,236 having different magnetic polarities is biasedly installed on the rotating body 234. Also, due to the biased rotation of the rotating body 234, magnetic vibration is generated. Preferably, several pairs of permanent magnets 35 may be provided in the therapeutic device.

Also, an electric connector 225 for applying an outside power source instead of the battery 232 is installed on the other wall of the internal case 220.

Figure 8:
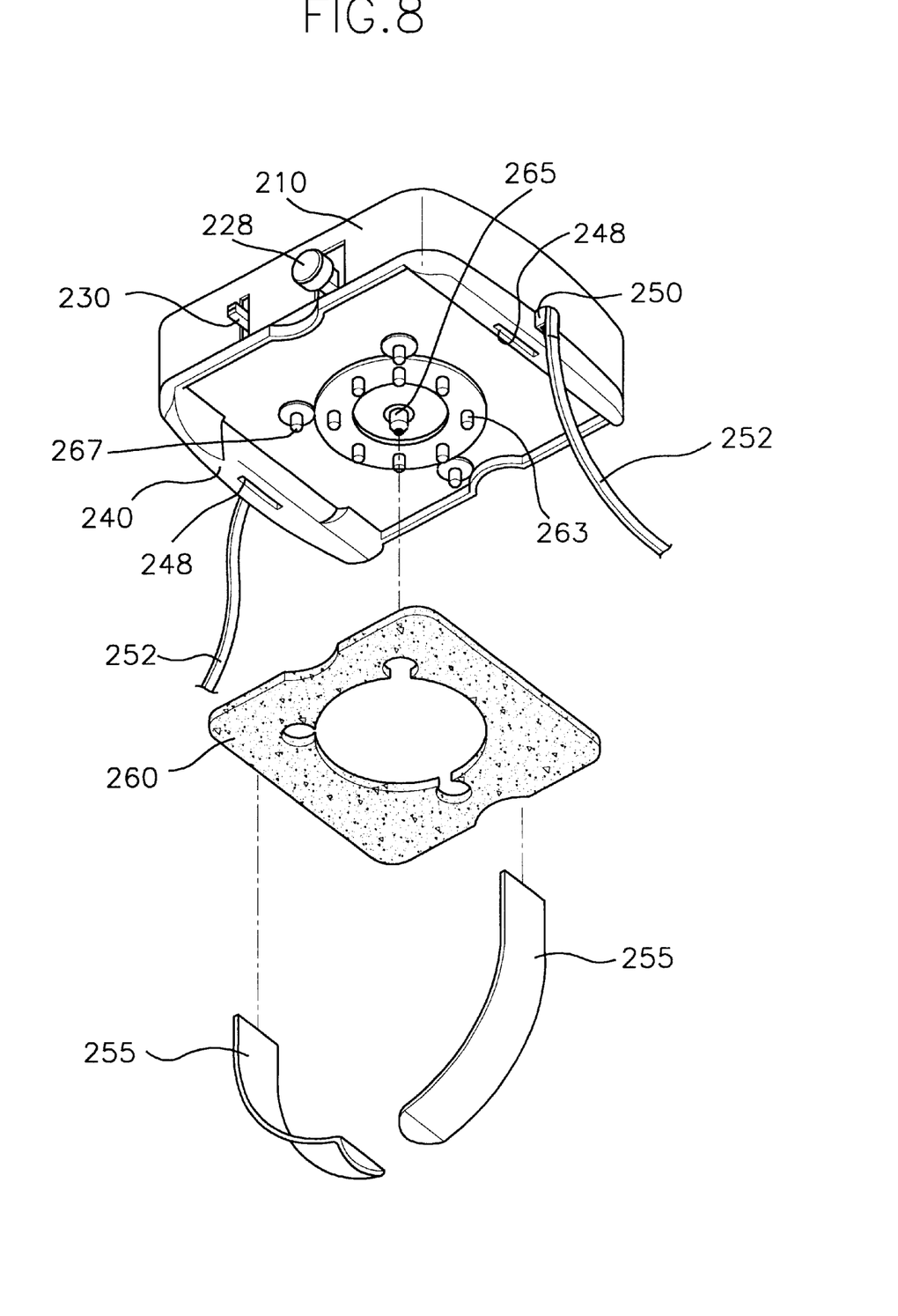
FIG. 8 is a bottom view according to FIG. 6.

FIG. 8 is a bottom view according to FIG. 6.

As shown in FIG. 8, a plurality of pressure bosses 263 and an electric needle 265 for electric stimulation are provided on the bottom central portion of the second case 240, and the electricity flows through the electric line 229 into the electric needle 265. Also, a plurality of radiation bulbs 267 for applying moxibustion-heat on a pain area of human body and displaying the operation of the therapeutic device 200 are installed on the bottom surface of the second case 220.

Furthermore, a combination 260 of the Macbanseok pieces for radiating far infrared rays is adhered to a bottom surface of the second case 240. The combination 260 is made by securely combining the Macbanseok pieces with adhesives.

Preferably, the combination 260 may be made from a mixture of the Macbanseok pieces, jade powder, and soil.

Hereinafter, the operation of the second preferred embodiment according to the present invention will be described.

When the on/off switch 230 is on in order to generate the magnetic vibration, the driving motor 224 operates, and the rotating body 234 having the permanent magnets 235,236 biasedly rotates. Each of the permanent magnets 235, 236 secured on the rotating body 234 generates magnetism different from each other, with a surface of one magnet 235 facing the skin of the human body having an N-pole and a surface of the other magnet 236 facing the skin having an S-pole.

Accordingly, when the rotating body 234 rotates, a continuous vibration is generated due to biased rotation. Also, the permanent magnets 235,236 alternatively impact on positive ions, negative ions, and iron in blood by means of alternate pulse-magnetic force. Thus, the alternate pulse-magnetic force reduces cholesterol in blood and facilitates blood circulation.

At the same time, the radiation bulbs 267 emit the moxibustion-heat for applying moxa to the skin.

Furthermore, when pressing the pressure button 228, the electricity is generated from the electricity generating source 226, and the electricity is transmitted through the electric line 229 to the electric needle 265. The transmitted electricity stimulates the pain area, resulting in providing the general acupuncture effect.

The radiation bulbs 267 emit heat, and the temperature around the combination 260 of the Macbanseok pieces is elevated. Therefore, the far infrared rays are radiated in proportion to the elevation of temperature from the combination 260 into the pain area, resulting in facilitating activation of systems in the human body and blood circulation.

The portable therapeutic device 200 may be worn on the pain area through the loops 252 connected to the eyes 250. Alternatively, the elastic bending plates 255 are separately secured in slits 248 formed at both sides of the second case 240. Thus, the therapeutic device 200 may be worn on the desired area of the human body through the bending plates 255. If not required, the bending plate 255 may be separated.

Embodiment 3

Hereinafter, a third preferred embodiment according to the present invention will be described.

In the third preferred embodiment according to the present invention, the illustration and the reference numbers of the same components with the components constructing the portable therapeutic device according to the second preferred embodiment of the present invention are similar with those of the second preferred embodiment.

The operation of the same components with the components constructing the portable therapeutic device according to the second preferred embodiment of the present invention is similar with that of the second preferred embodiment.

Figure 9:
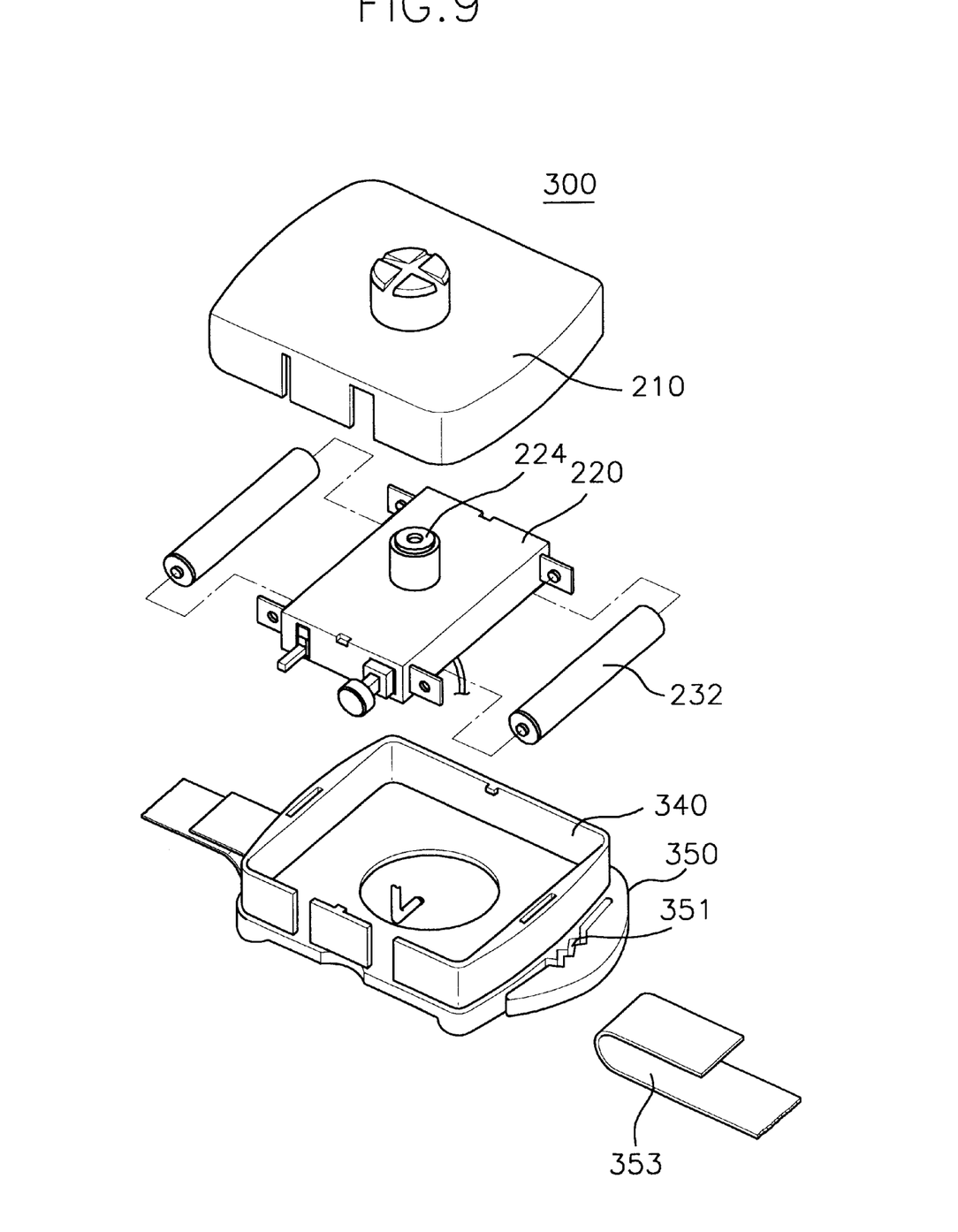
FIG. 9 is an exploded perspective view of a portable therapeutic device according to a third preferred embodiment of the present invention.

FIG. 9 is an exploded perspective view of a portable therapeutic device according to a third preferred embodiment of the present invention.

As shown in FIG. 9, a portable therapeutic device 300 according to a third preferred embodiment of the present invention has protrusions 350 integrally formed at both side walls of a second case 340, and a zigzag groove 351 is formed in each protrusion 350. A band 353 is inserted in the zigzag groove 351, and the portable therapeutic device 300 is easily worn and separated, to and from the desirable area of the human body by a band 353.

The band 353 does not easily come undone due to friction resistance of the zigzag groove 351.

As mentioned above, the portable therapeutic device according to the present invention radiates far infrared rays from the Macbanseok pieces received therein and applies electric stimulation to the body by means of an electric needle, in addition to generating magnetic vibration through rotation of two permanent magnets having magnetic polarities different from each other. Also, the portable therapeutic device is convenient to carry and use.

Accordingly, the portable therapeutic device smoothes blood circulation by means of the magnetic vibration, and may relieve a pain of diseases such as migraine, tonsillitis, bronchitis, arthritis, shoulder pain, enlargement of the prostate gland, premature ejaculation, itching, hemorrhoids, and indisposition of the peripheral nerve.

While this invention has been specifically shown and described with reference to the particular embodiments thereof, it will be understood by those skilled in the art that various changes in form and detail may be effected therein without departing from the spirit and scope of the invention as defined by the appended claims.

What is claimed is:

1. A portable therapeutic device comprising:
    a first case, the first case comprising:
        a top surface having a central hole, a plurality of acupressure bosses for massaging the human body, a plurality of penetrating holes for directly transmitting the far infrared rays on the human body, and a translucent plate having a radiation bulb and mounted on the central hole;
        a cylindrical side wall vertically elongated from a periphery of the top surface; and
        inner separating walls for forming a battery housing, a magnetic vibration generating means housing, and a Macbanseok housing;
    a second case joined with the first case;
    a power supply means mounted in the first case and the second case and having a battery for supplying power, a first terminal contacting with one end of the battery, and a second terminal contacting with the other end of the battery;
    a magnetic vibration generating means which generates vibration and alternate magnetic force by rotation of the rotating body, and has at least one pair of permanent magnets generating a magnetism with a magnetic polarity of a magnet surface opposite human body skin being different from each other, rotating body biasedly receiving the permanent magnets, and a driving motor for operating the rotating body through power transmitted from the power supply means; and
    a means for generating far infrared rays through internal heat produced by the operation of the driving motor in order to facilitate blood circulation of human body.

2. A portable therapeutic device comprising:
    a first case, the first case comprising:
        a top surface having a central hole, a plurality of acupressure bosses for massaging the human body, a plurality of penetrating holes for directly transmitting the far infrared rays on the human body, and a translucent plate having a radiation bulb and mounted on the central hole;
        a cylindrical side wall vertically elongated from a periphery of the top surface; and
        inner separating walls for forming a battery housing, a magnetic vibration generating means housing, and a Macbanseok housing;
    a second case joined with the first case; said second case has two stoppers projected from an inner side wall of the second case into the center of the second case, and a supporting plate for supporting the battery is installed between the two stoppers;
    a power supply means mounted in the first case and the second case and having a battery for supplying power, a first terminal contacting with one end of the battery, and a second terminal contacting with the other end of the battery;
    a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means; and
    a means for generating far infrared rays through internal heat produced by the operation of the driving motor in order to facilitate blood circulation of human body.

3. A portable therapeutic device comprising:
    a first case, the first case comprising:
        a top surface having a central hole, a plurality of acupressure bosses for massaging the human body, a plurality of penetrating holes for directly transmitting the far infrared rays on the human body, and a translucent plate having a radiation bulb and mounted on the central hole;
        a cylindrical side wall vertically elongated from a periphery of the top surface; and
        inner separating walls for forming a battery housing, a magnetic vibration generating means housing, and a Macbanseok housing;
    a second case joined with the first case; wherein said second case has two stoppers projected from an inner side wall of the second case into the center of the second case, and a supporting plate for supporting the battery is installed between the two stoppers;
    a power supply means mounted in the first case and the second case and having a battery for supplying power, a first terminal contacting with one end of the battery, and a second terminal contacting with the other end of the battery; the second terminal is biasedly installed at one portion of the supporting plate;

a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means; and a means for generating far infrared rays through internal heat produced by the operation of the driving motor in order to facilitate blood circulation of human body.

4. A portable therapeutic device comprising:

a first case;

a second case joined with the first case;

a power supply means mounted in the first case and the second case and having a battery for supplying power, a first terminal contacting with one end of the battery, and a second terminal contacting with the other end of the battery;

a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means; and a means for generating far infrared rays through internal heat produced by the operation of the driving motor in order to facilitate blood circulation of human body, wherein the far infrared rays generating means includes Macbanseok pieces.

5. A portable therapeutic device comprising:

a first case;

a second case joined with the first case;

a power supply means mounted in the first case and the second case and having a battery for supplying power, a first terminal contacting with one end of the battery, and a second terminal contacting with the other end of the battery;

a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means;

a means for generating far infrared rays through internal heat produced by the operation of the driving motor in order to facilitate blood circulation of human body; and an electricity generating means including:

a pressure button;

an electricity generating source generating electricity through push of the pressure button;

an electricity output terminal formed at one portion of the electricity generating source for emitting the electricity;

an electric needle projectingly formed outside the first case for directly transmitting the electricity to the human body; and an electric line transmitting the electricity from the electricity output terminal into the electric needle.

6. The portable therapeutic device according to claim 5, further comprising an electric connector for connecting an outside power source.

7. A portable therapeutic device comprising:

a first case;

a second case joined with the first case and having a plurality of radiation bulbs for displaying the operation of the magnetic vibration generating means and radiating moxibustion-heat;

a power supply means mounted in the first case and the second case and having a battery for supplying power, and terminals contacting with the battery;

a magnetic vibration generating means which generates vibration and alternate magnetic force by rotation of the rotating body, and has at least one pair of permanent magnets generating a magnetism with a magnetic polarity of a magnet surface opposite human body skin being different from each other, a rotating body biasedly receiving the permanent magnets, and a driving motor for operating the rotating body through power transmitted from the power supply means; and a means for generating far infrared rays through internal heat produced by the operation of the driving motor and the plurality of radiation bulbs in order to facilitate blood circulation of human body.

8. The portable therapeutic device according to claim 7, wherein the second case includes a plurality of acupressure bosses circularly arranged at equal intervals.

9. The portable therapeutic device according to claim 7, wherein the far infrared rays generating means is installed on a bottom surface of the second case.

10. The portable therapeutic device according to claim 9, wherein the far infrared rays generating means includes an adhered body having Macbanseok pieces.

11. The portable therapeutic device according to claim 9, wherein the far infrared rays generating means includes an adhered body having Macbanseok pieces, jade powder, and soil.

12. The portable therapeutic device according to claim 7, wherein the second case includes two protrusions integrally formed at both ends, and each of the protrusions has a zigzag groove.

13. The portable therapeutic device according to claim 7, further comprising an on/off switch for operation of the magnetic vibration generating means.

14. The portable therapeutic device according to claim 7, further comprising an electric connector for connecting an outside power source.

15. The portable therapeutic device according to claim 7, further comprising an electricity generating means including:

a pressure button;

an electricity generating source generating electricity through push of the pressure button;

an electricity output terminal formed at one portion of the electricity generating source for emitting the electricity;

an electric needle projectingly formed outside the first case for directly transmitting the electricity to the human body; and an electric line transmitting the electricity from the electricity output terminal into the electric needle.

* * * * *